United States Patent [19]

Laviero

[11] Patent Number: 4,932,089
[45] Date of Patent: Jun. 12, 1990

[54] BEACH PILLOW

[76] Inventor: Frank D. Laviero, 341 Divinity St., Bristol, Conn. 06010

[21] Appl. No.: 388,589

[22] Filed: Aug. 2, 1989

[51] Int. Cl.$^5$ .......................... A47C 21/04; A61F 7/00
[52] U.S. Cl. ............................................. 5/421; 5/441;
5/442; 128/376
[58] Field of Search .................. 5/419, 421, 441, 442;
297/180; 383/901; 62/261; 128/376, 403

[56] References Cited

U.S. PATENT DOCUMENTS

| 2,521,780 | 9/1950 | Dodd | 5/441 |
| 2,612,645 | 10/1952 | Boland | 5/441 |
| 2,783,807 | 3/1957 | Duffield | 128/403 X |
| 2,976,700 | 3/1961 | Jackson | 297/180 X |
| 3,840,918 | 10/1974 | Shave | 128/403 X |
| 4,060,276 | 11/1977 | Lindsay | 5/421 X |
| 4,528,705 | 7/1985 | Greenwalt | |
| 4,783,866 | 11/1988 | Simmons et al. | 5/421 X |
| 4,805,619 | 2/1989 | Swearingen | 383/901 X |

FOREIGN PATENT DOCUMENTS 931649 7/1963 United Kingdom .................... 5/421

Primary Examiner—Michael F. Trettel

[57] ABSTRACT

An air-inflatable beach pillow having a wedge-shaped cross section. An ice water container extends transversely across the inclined upper surface of the pillow to cool the neck area of the person whose head is resting on the pillow's surface.

1 Claim, 1 Drawing Sheet

BEACH PILLOW

BACKGROUND AND SUMMARY OF THE INVENTION

This invention relates to a beach pillow having an ice water container built into the pillow's upper surface. A person lying on the beach can rest his/her head on the pillow, with the back of the neck in close proximity to the ice water container, thereby, enabling the person to experience a pleasant cooling sensation on the blood vessels in the neck.

The pillow preferably has a wedge-shaped cross-sectional configuration that provides an inclined head-engaging surface; the pillow is an air-inflatable structure. In certain respects the pillow of this invention is similar to air-inflatable pillows shown in U.S. Pat. Nos. 2,612,645 and 4,528,705. My improved pillow includes a self-contained ice water container not disclosed in the referenced patents.

THE DRAWINGS

DESCRIPTION OF A PREFERRED EMBODIMENT OF THE INVENTION

Figure 1:
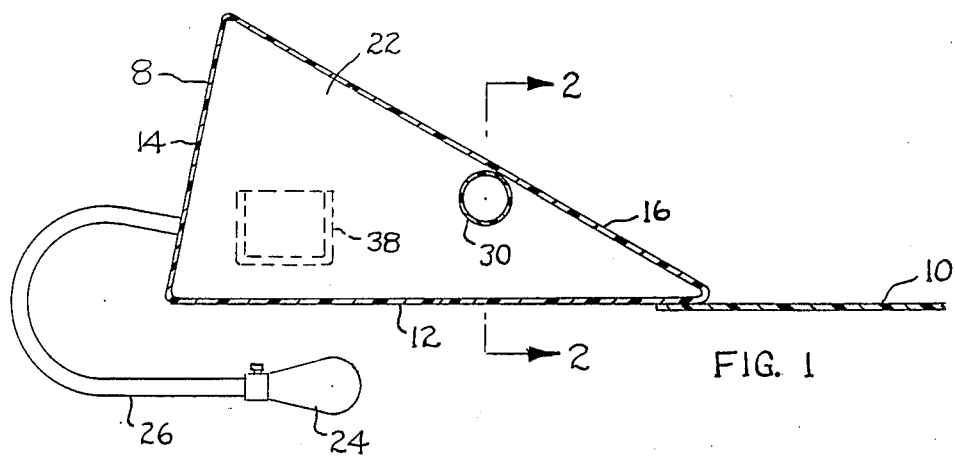
FIG. 1 is a sectional view taken through a pillow constructed according to the invention.
Figure 2:
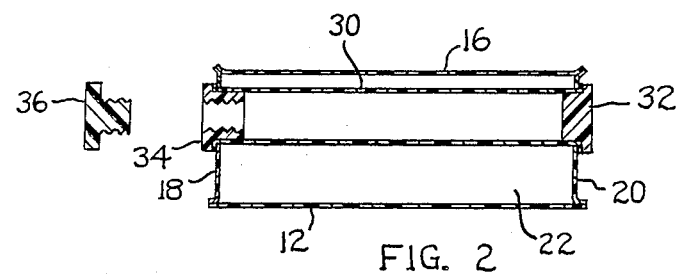
FIG. 2 is a sectional view on line 2—2 in FIG. 1.

FIG. 1 shows a beach pillow 8 having a triangular cross section. The pillow may be attached to an elongated rectangular panel 10 for placement on a sand beach surface to underlie the body of a person lying in a prone position; the person's head will be slightly inclined in accordance with the inclination angle of the pillow's upper surface.

Pillow 8 is comprised of a bottom panel 12, upstanding rear panel 14 extending from the rear end edge of panel 12, and an inclined upper panel 16 extending from the other front end edge of panel 12. Triangular shaped side panels 18 and 20 close the side edges of panels 12, 14 and 16, thereby forming a sealed air space 22. Air can be pumped into space 22 by manually squeezing a small air pump device 24; an air hose 26 connects the pump to sealed space 22.

A tubular ice water container 30 extends transversely along the inclined upper panel 16 at a point near the front edge of the panel. The location of container 30 is selected so that the container will be in near proximity to the person's neck when his/her head rests on panel 16. Container 30 may be formed out of a flexible hollow tube closed at one end by a cap 32. The other end of the tube may be connected to an annular collar 34 that is attached to pillow side panel 18. A screw cap 36 can be screwed into the collar 34 mouth to seal the tubular container against escape of cold water.

Tubular container 30 may be filled (or partially filled) with a mixture of ice and water prior to adding inflation air into space 22. When the person lays his/her head on the inflated pillow the cold surface of tubular container 30 will provide a cooling action on the blood vessels in the person's neck. This is especially desirable when the pillow is used at the beach on a hot summer day.

The usefulness of the pillow may be enhanced by the provision of pockets 38 on the outer surface(s) of side panel 18 or 20. Such pockets can be used to store cigarettes, sun tan lotion, etc.

I claim:

1. An air-inflatable beach pillow having a wedge-shaped cross section; said pillow comprising a horizontal bottom panel (12) having a front edge, a rear edge, and two side edges; an inclined panel extending upwardly and rearwardly from the front edge of said bottom panel; an upstanding rear panel (14) extending upwardly from the rear edge of said bottom panel to connect with the inclined panel; said inclined panel and rear panel having side edges located in a common vertical plane with the side edges of the bottom panel; triangular side panels (18 and 20) closing the side edges said bottom panel, rear panel and inclined panel; said inclined panel having an exposed upper surface adapted to supportably engage the head and neck area of a person resting against the pillow, and an undersurface facing the closed interior space defined by the panels; a hollow flexible tube (30) extending from one side panel to the other side panel in near adjacency to the undersurface of the inclined panel; said flexible tube being located at an intermediate point between the front and rear edges of the pillow so that the flexible tube is in near proximity to the person's neck; said flexible tube having a first end thereof sealably attached to said one side panel and a second end thereof sealably attached to the other side panel; a cap (32) closing said first end of the flexible tube; an annular collar (34) extending within said second end of said flexible tube; a second cap (36) removably fitting into said annular collar to close said second end of the flexible tube; and means (at 24, 26) for introducing pressurized air into the interior space defined by said panels, whereby the pillow is inflated to a condition for cushionably supporting the head and neck area of a person resting on the beach; said flexible tube being adapted to receive ice water therein, so as to cool the upper surface of the inclined panel that comes in contact with the person's neck.

* * * * *